(12) United States Patent
Singh et al.

(10) Patent No.: US 9,101,546 B2
(45) Date of Patent: Aug. 11, 2015

(54) CAPSULE FOR ENCAPSULATING A TABLET

(71) Applicant: SCI-TECH CENTRE, Mumbai, Maharashtra (IN)

(72) Inventors: Jasjit Singh, Maharashtra (IN); Prakash Deshmukh, Maharashtra (IN); Thomas Rodrigues, Maharashtra (IN)

(73) Assignee: SCI-TECH CENTRE, Mumbai, Maharashtra (IN)

( * ) Notice: Subject to any disclaimer, the term of this patent is extended or adjusted under 35 U.S.C. 154(b) by 0 days.

(21) Appl. No.: 14/372,355

(22) PCT Filed: Sep. 17, 2013

(86) PCT No.: PCT/IN2013/000561
§ 371 (c)(1),
(2) Date: Jul. 15, 2014

(87) PCT Pub. No.: WO2014/049606
PCT Pub. Date: Apr. 3, 2014

(65) Prior Publication Data
US 2014/0348912 A1    Nov. 27, 2014

(30) Foreign Application Priority Data
Sep. 28, 2012   (IN) .......................... 2874/MUM/2012

(51) Int. Cl.
*A61K 9/48*   (2006.01)

(52) U.S. Cl.
CPC .................................. *A61K 9/4808* (2013.01)

(58) Field of Classification Search
CPC .................................................. A61K 9/4808
See application file for complete search history.

(56) References Cited

U.S. PATENT DOCUMENTS

| 3,508,678 A | 4/1970 | Graham et al. |
| 3,823,843 A | 7/1974 | Stephens et al. |
| 5,795,588 A | 8/1998 | Sauter |
| 2004/0253312 A1 | 12/2004 | Sowden et al. |
| 2007/0190131 A1 | 8/2007 | Perry |

FOREIGN PATENT DOCUMENTS

WO    2008/072956 A1    6/2008

OTHER PUBLICATIONS

United States Patent and Trademark Office (ISR/US), "International Search Report", US, Apr. 9, 2014.

*Primary Examiner* — Aradhana Sasan
(74) *Attorney, Agent, or Firm* — Tim Tingkang Xia, Esq.; Locke Lord LLP (57) ABSTRACT

A capsule for encapsulating a tablet, includes two capsule portions of equal sizes and dimensions, each containing a moisture content of 12 to 16% and having a plurality of ridges projecting inwardly from the inner circumference of the respective capsule portions and extending along the inner circumference of the respective capsule portions in radially spaced apart relationship with one another and defining fluid flow passages between the ridges. The outline defined by the tips of the ridges correspond to the outer surface of the tablet to provide an interference fit between the ridges and the tablet when the capsule portions are push fitted over the tablet from the ends of the tablet in an abutting but not overlapping relationship with each other at ambient conditions.

15 Claims, 10 Drawing Sheets

CAPSULE FOR ENCAPSULATING A TABLET

FIELD OF THE INVENTION

This invention relates to a capsule for encapsulating a tablet.

BACKGROUND OF THE INVENTION

Orally administered tablets of medications or medical preparations including neutraceuticals or neutraceutical preparations are often bitter or have unpleasant taste and are very difficult and uncomfortable to swallow because of the bitter or unpleasant taste. In order to mask the unpleasant or bitter taste of the tablets and to make the tablets easy and convenient to swallow, they are often covered with a palatable coating or optionally covered with a palatable coating and encapsulated in capsules.

Sauter describes encapsulation of elongated, substantially cylindrical, solid objects within gelatin capsules or coverings comprising pairs of capsule portions. The capsule portions with their open ends are positioned facing towards the ends of the objects and are relatively moved onto the objects into a position in which the open ends of the capsule portions are in abutting but not overlapping relationship with each other. The capsule portions are dried on the objects to reduce the moisture content from about 10% to about 25% when the objects are encapsulated. Thereafter, the drying is continued to shrink the capsule portions into a tight fitting relationship with the objects (U.S. Pat. No. 5,511,361). Sauter also describes encapsulation of cylindrical caplets with gelatin capsule halves, in which the gelatin capsule halves containing a moisture content of 18-20% are introduced over the ends of the caplets in abutting but not overlapping relationship with each other and are subsequently allowed to dry and shrink fit tightly on to the caplets (U.S. Pat. No. 5,609,010).

In both the above prior art teachings, air will get invariably entrapped in the capsules during encapsulation and due to the air pressure developed in the capsules, the capsules may get damaged. Furthermore, the capsules are likely to get deformed during encapsulation due to the moisture content in the capsule portions being high thereby damaging the capsules and/or spoiling the shape and size and aesthetic look of the capsules. Since the moisture content in the capsules is high during encapsulation, the capsules are also not suitable for encapsulation of hygroscopic or hydrophilic tablets. The capsules require drying during encapsulation and also after the encapsulation to ensure a shrink fit on the tablets. This is not only inconvenient and cumbersome to carry out but also requires considerable amount of energy. Besides, the production time is increased and productivity is reduced. On coming into contact with the body fluids in the stomach, the body fluids will enter the capsules through the hairline gap (capillary opening) between the abutting ends of the capsule portions and slowly flow into the capsules. Therefore, the disintegration and dissolution of the tablets will be slow.

Amey et al describe encapsulation of caplets in capsules. Encapsulation comprises filling atleast one capsule part with one or more caplets, wherein the clearance between the capsule part and the caplet is in the range of −0.5 to 0.5 mm. Capsule parts are put together and treated by cold shrinking. Empty capsule parts are either kept after production at humid conditions in the range of about 40 to about 90% relative humidity to retain a moisture content in the range of about 14 to about 19% by weight of the capsule shell or are re-humidified to said moisture content before feeding into a capsule filling machine. The capsule parts are kept under above humid conditions within the filling machine during rectifying and assembling with the caplet having a moisture content in the range of about 0 to about 12% by weight. The encapsulated dosage form is dried at a relative humidity in the range of about 20 to about 40% and a temperature in the range of about 15 to about 60° C. to shrink fit on the caplets (U.S. Pat. No. 6,245,350).

In the case of the above prior art teaching also, air is likely to get trapped in the capsule during encapsulation and the capsule may get damaged. Due to the clearance between the caplets and capsule parts also, the capsule parts may collapse on the caplets and get deformed and damaged. As the moisture content in the capsule portions being high during encapsulation, they are prone to get damaged and/or deformed during encapsulation thereby affecting the shape and size and aesthetic look of the capsules. The capsules are also not suitable for encapsulating hygroscopic tablets because of the high moisture content in the capsule parts. On coming into contact with the body fluids in the stomach, the body fluids will enter the capsules through the hairline gap between the abutting ends of the capsule portions and slowly flow into the capsules thereby slowing down the disintegration and dissolution of the tablets. The capsules require drying after encapsulation to ensure a shrink fit on the tablets. Due to drying energy requirement for encapsulation of the tablets increases. Further the production time increases and productivity reduces. It is also difficult and cumbersome to maintain the humidity conditions required in the above prior art teaching.

DETAILED DESCRIPTION OF THE INVENTION

According to the invention there is provided a capsule for encapsulating a tablet, comprising two capsule portions of equal sizes and dimentions, wherein the capsule portions contain a moisture content of 12 to 16% and the capsule portions each comprises interference fit means at the inner circumference thereof having a plurality of fluid flow passages therethrough and providing an interference fit between the capsule portions and the tablet when the capsule portions are push fitted over the tablet from the ends of the tablet in an abutting but not overlapping relationship with each other at ambient conditions.

DESCRIPTION OF EMBODIMENTS OF THE INVENTION

Figure 1:
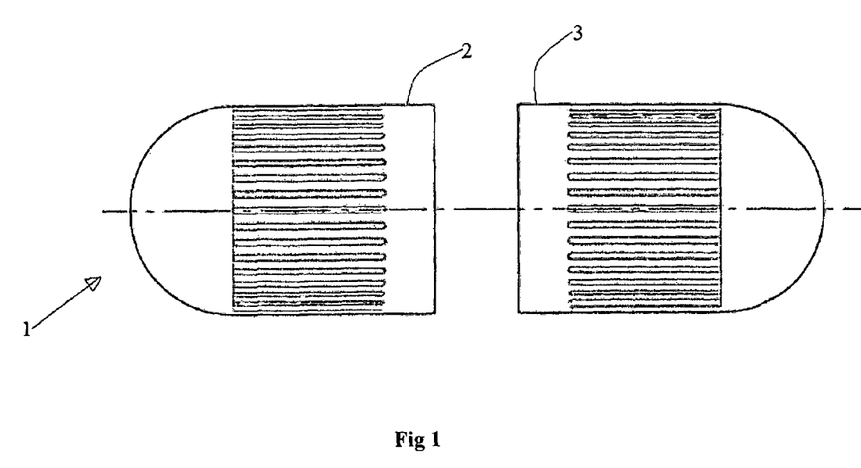
FIGS. 1 and 2 of the drawings accompanying the provisional specification are schematic elevation and longitudinal section of the two capsule portions of a capsule according to an embodiment of the invention, respectively.
Figure 2:
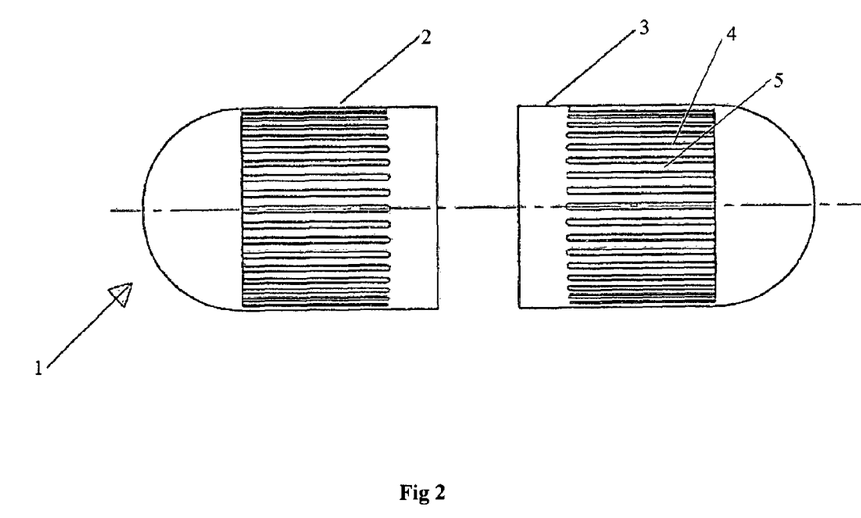
Figure 3:
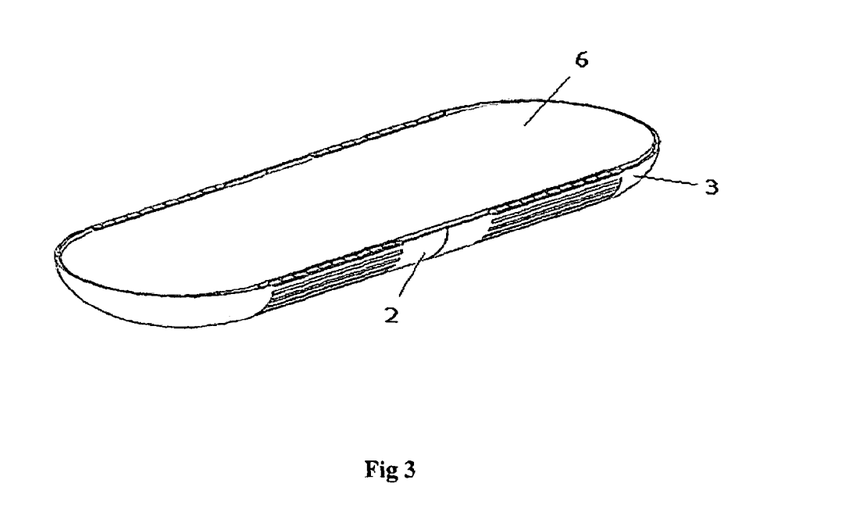
FIG. 3 of the drawings accompanying the provisional specification is a schematic longitudinal section of the capsule of FIGS. 1 and 2 encapsulated with a tablet.

As illustrated in FIGS. 1 to 3 of the drawings accompanying the provisional specification, 1 is a capsule comprising two capsule portions 2 and 3 of equal and dimensions and containing a moisture content of 12-16%, preferably 12.5 to 14.5% and preferably made from gelatin, cellulose or starch. However, it is to be clearly understood that the capsule portions can be made of any other capsule forming material or composition. Each of the capsule portions comprises a plurality of ridges 4 projecting inwardly from the inner circumference of the respective capsule portions and extending along the inner circumference of the respective capsule portions in radially spaced apart relationship with one another and defining fluid flow passages 5 between the ridges.

The outline defined by the tips of the ridges correspond to the outer surface of a tablet 6 encapsulated in the capsule by push fitting the capsule portions over the tablet from the ends of the tablet in an abutting but not overlapping relationship with each other (FIG. 3). The encapsulation is carried out at ambient conditions of about 20-25° C. The encapsulated tablets are stored at desired or recommended storage conditions. Preferably the encapsulated tablets are stored at 15-30° C. and at 40-65% humidity. The ridges provide an interference fit between the capsule portions and the tablet when the capsule portions are push fitted over the tablet, besides describing fluid flow passage therebetween.

Figure 4:
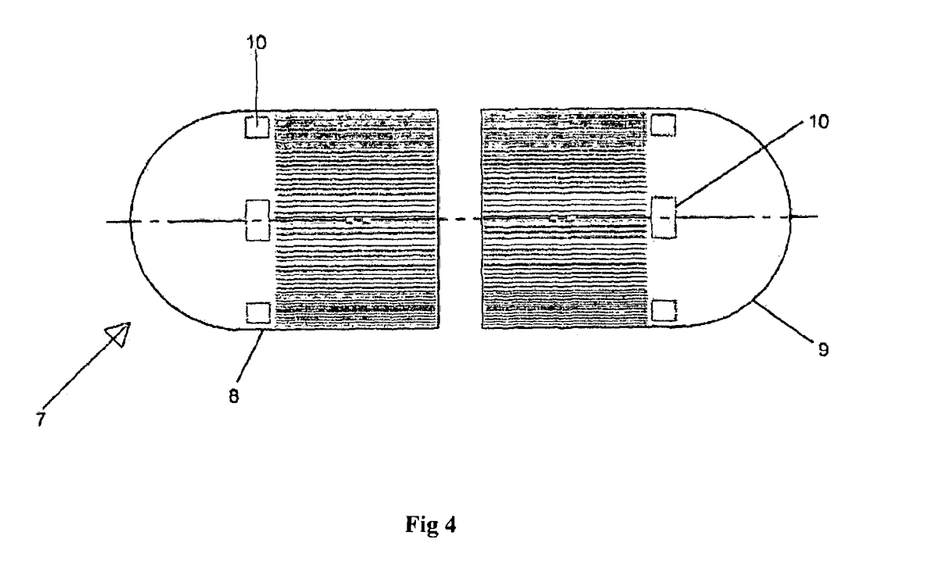
FIGS. 4 and 5 of the drawings accompanying the provisional specification are schematic elevation and longitudinal section of the two capsule portions of a capsule according to another embodiment of the invention, respectively.
Figure 5:
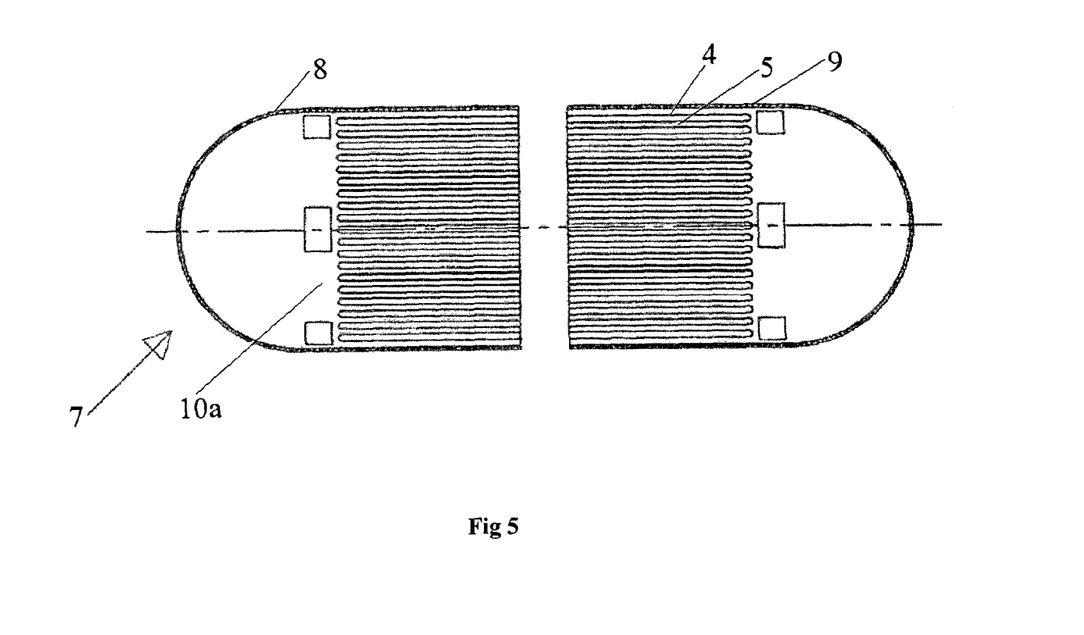
Figure 6:
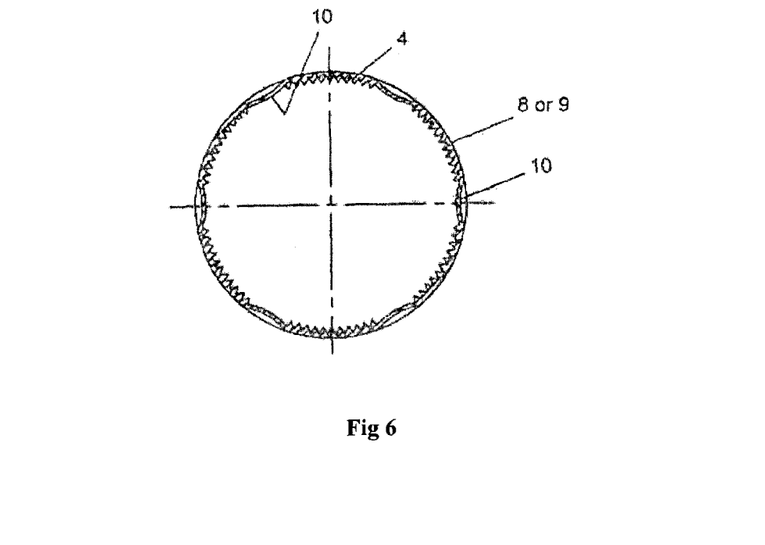
FIG. 6 of the drawings accompanying the provisional specification is a schematic sectional view of either of the two capsule portions of FIGS. 4 and 5.

The capsule 7 as illustrated in FIGS. 4 to 6 of the drawings accompanying the provisional specification comprises two capsule portions 8 and 9. Each of the capsule portions further comprises a plurality of bulges 10 projecting inwardly from the inner circumference of the respective capsule portions in the proximity of the ridges at the crown side of the capsule portions and in radially spaced apart relationship with one another. The outline defined by the centre of the bulges corresponds to the outline defined by the tips of the ridges to provide further interference fit between the bulges and the tablet when the capsule portions are push fitted over the tablet. The spaces between the bulges define further fluid flow passages.

Figure 7:
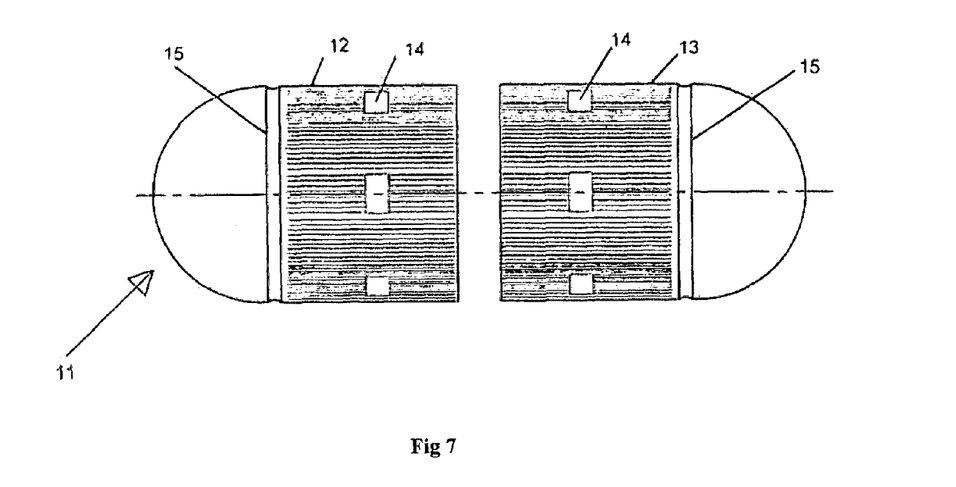
FIGS. 7 and 8 of the drawings accompanying the provisional specification are schematic elevation and longitudinal section of the two capsule portions of a capsule according to another embodiment of the invention, respectively.
Figure 8:
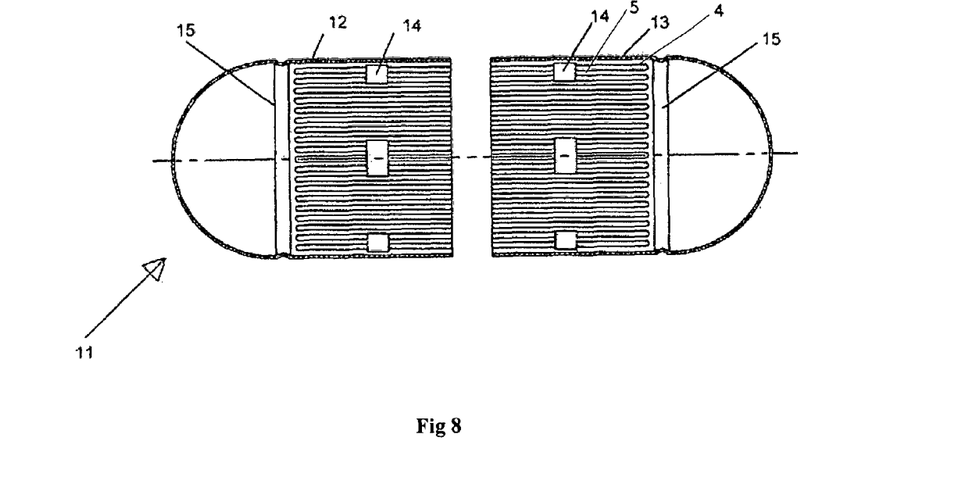

In the embodiment illustrated in FIGS. 7 and 8 of the drawings accompanying the provisional specification, the capsule 11 comprises two capsule portions 12 and 13 with bulges 14 at an intermediate position of the ridges. Each of the capsule portions further comprises a circular protrusion 15 protruding inwardly from the inner circumference of the capsule portions at the crown side of the capsule portions in the proximity of the ridges. The outlines defined by the centre of the bulges and the centre of the circular protrusion correspond to the outline defined by the tips of the ridges to provide a further interference fit between the bulges and the circular protrusion and the tablet when the capsule portions are push fitted over the tablet. The spaces between the bulges also define fluid flow passages.

Figure 9:
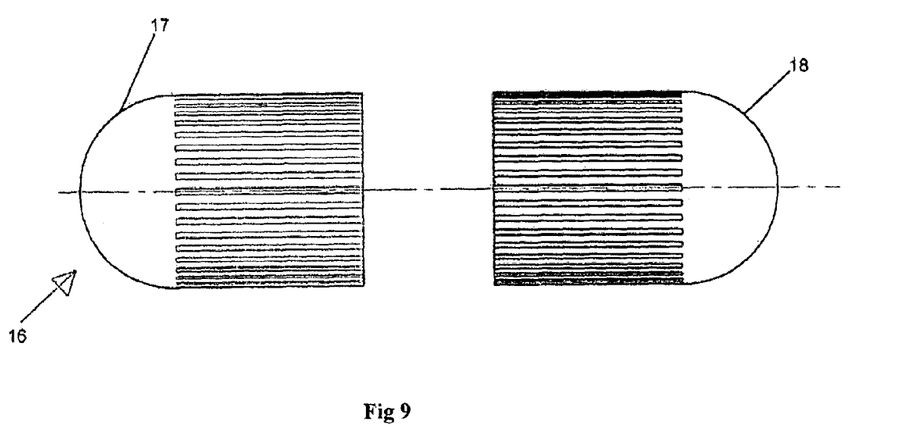
FIGS. 9 and 10 of the drawings accompanying the provisional specification are schematic elevation and longitudinal section of the two capsule portions of a capsule according to another embodiment of the invention, respectively.
Figure 10:
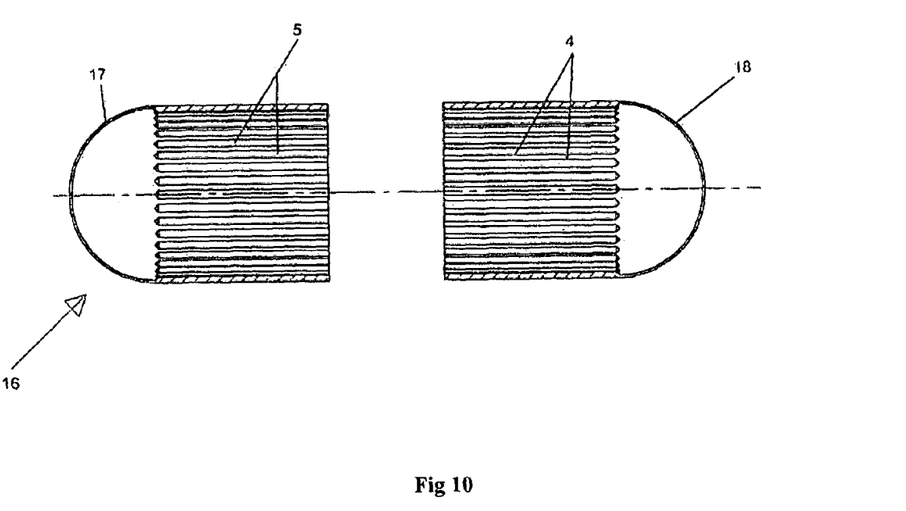
Figure 11:
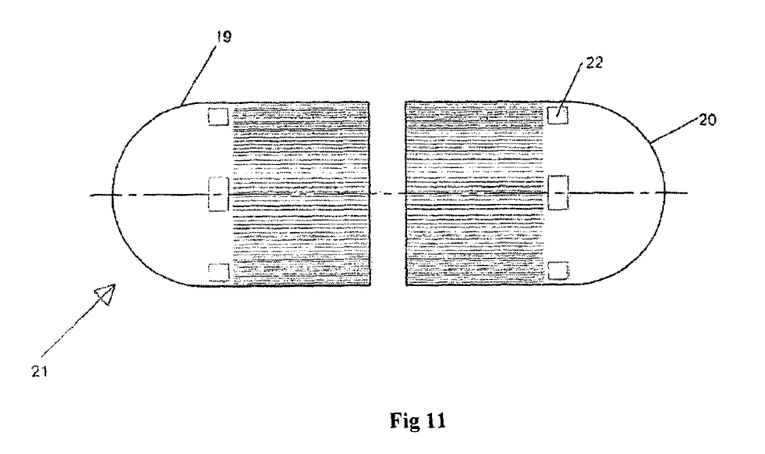
FIGS. 11 and 12 of the drawings accompanying the provisional specification are schematic elevation and longitudinal section of the two capsule portions of a capsule according to another embodiment of the invention, respectively.
Figure 12:
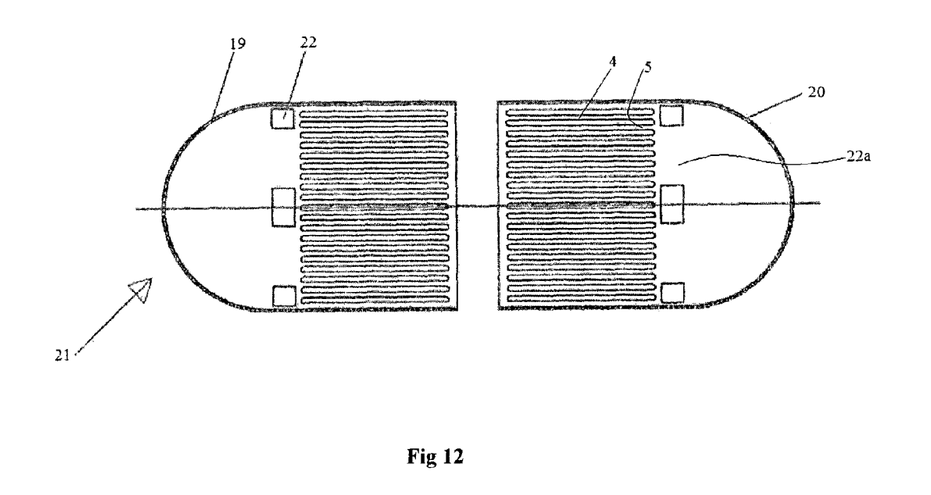

In the embodiment illustrated in FIGS. 9 and 10 of the drawings accompanying the provisional specification, the capsule 16 comprises two capsule portions 17 and 18 each having ridges 4 along the inner circumference of the capsule portions extending upto the edge of the open end of the respective capsule portions to define fluid flow passages between the ridges extending upto the edge of the open end of the respective capsule portions. As illustrated in FIGS. 11 and 12 of the drawings accompanying the provisional specification, each of the capsule portions 19 and 20 of capsule 21 further comprises a plurality of bulges 22 projecting inwardly from the inner circumference of the respective capsule portions in the proximity of the plurality of the ridges at the crown side of the capsule portions and in radially spaced apart relationship with one another. The outline defined by the centre of the bulges correspond to the outline defined by the tips of the ridges to provide a further interference fit between the capsule portions and the tablet when the capsule portions are push fitted over the tablet. The spaces between the bulges define further fluid flow passages.

Figure 13:
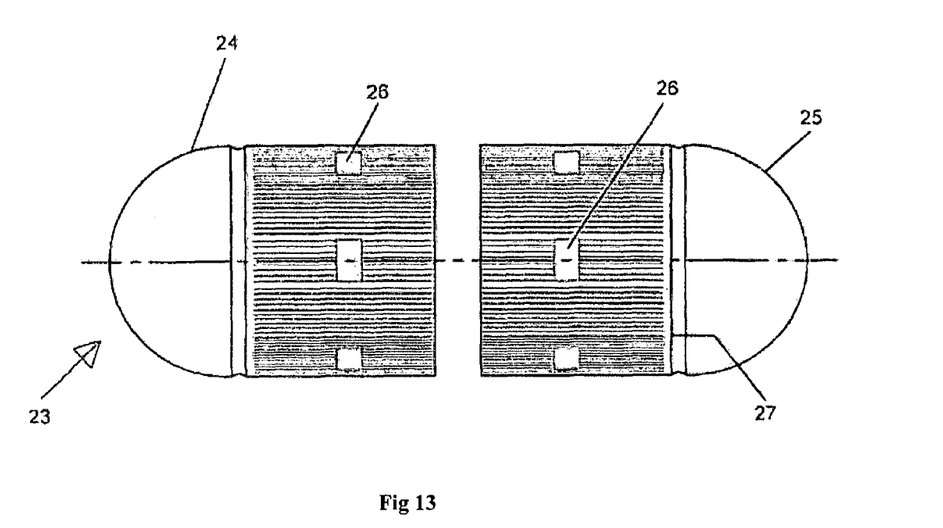
FIGS. 13 and 14 of the drawings accompanying the provisional specification are schematic elevation and longitudinal section of the two capsule portions of a capsule according to another embodiment of the invention, respectively.
Figure 14:
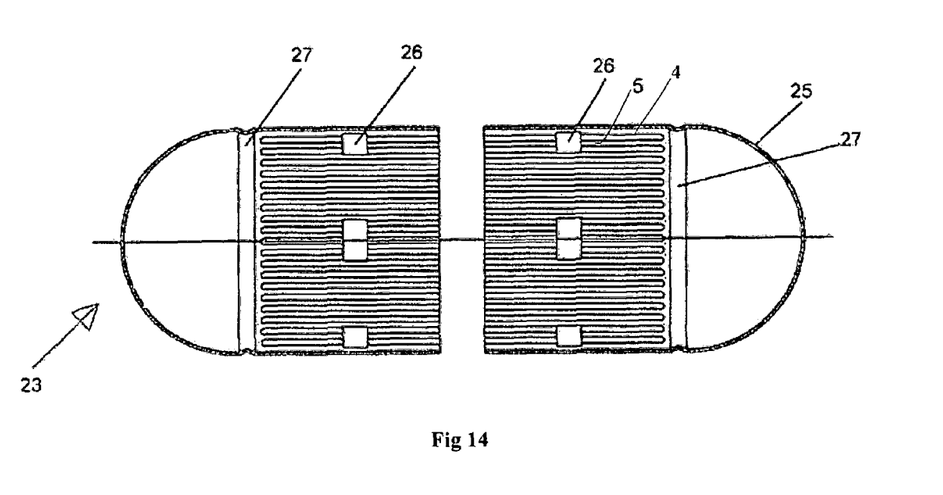

The capsule 23 as illustrated in FIGS. 13 and 14 of the drawings accompanying the provisional specification comprises two capsule portions 24 and 25. Each of the capsule portions further comprises a plurality of bulges 26 projecting inwardly from the inner circumference of the respective capsule portions at an intermediate position of the ridges in radially spaced apart relationship with one another. 27 is a circular protrusion protruding inwardly from the inner circumference of the capsule portions at the crown side of the respective capsule portions. The outlines defined by the centre of the bulges and centre of the circular protrusion correspond to the outline defined by the tips of the ridges to provide further interference fit between the bulges and circular protrusion and the tablet when the capsule portions are push fitted over the tablet. The spaces between the bulges also define fluid flow passages.

Figure 15:
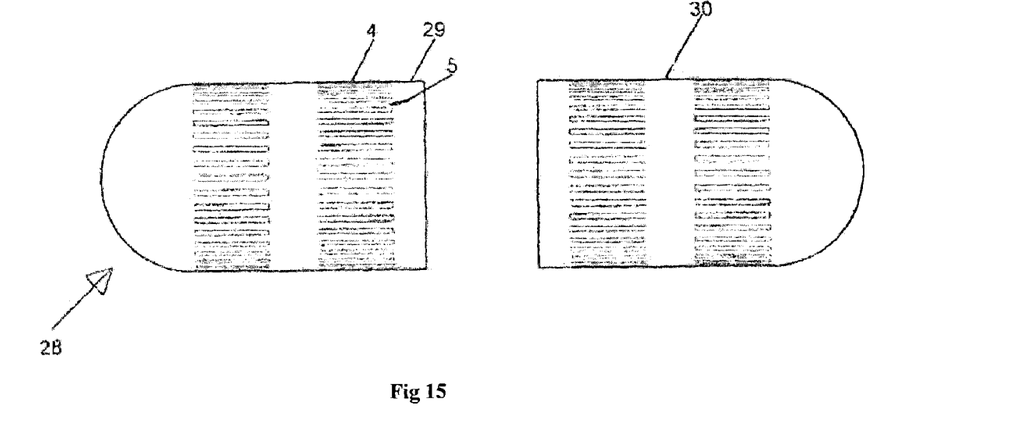
FIGS. 15 and 16 of the drawings accompanying the provisional specification are schematic elevation and longitudinal section of the two capsule portions of a capsule according to another embodiment of the invention, respectively.
Figure 16:
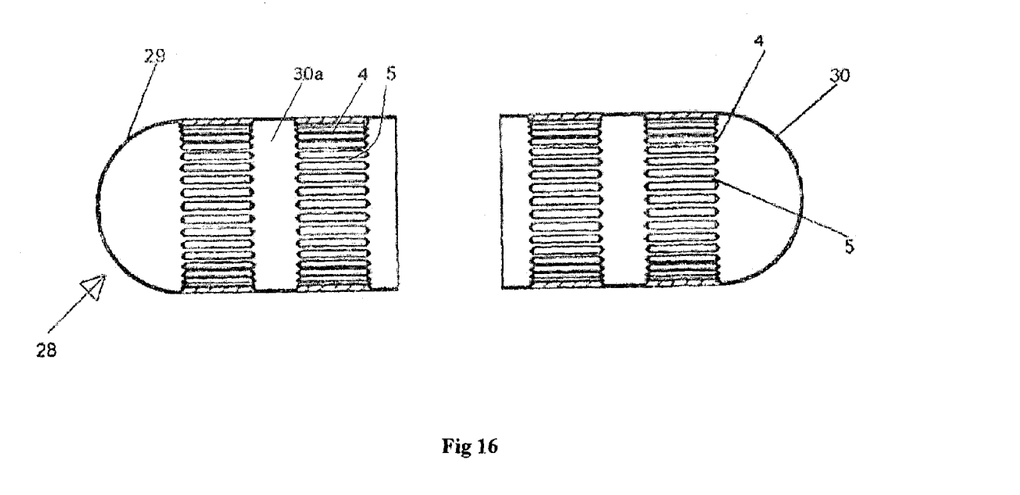

The capsule 28 as illustrated in FIGS. 15 to 16 of the drawings accompanying the provisional specification comprises two capsule portions 29 and 30. Each of the capsule portions comprises two sets of ridges 4 at the inner circumference of the respective capsule portions spaced apart from each other along the length of the inner circumference of the capsule portions. Each set of ridges comprises a plurality of ridges projecting inwardly from the inner circumference of the respective capsule portions in radially spaced apart relationship with one another and defining fluid flow passages 5 between the ridges. The outline defined by the tips of each set of ridges corresponding to the outer surface of the tablet to provide further interference fit between the ridges and the tablet when the capsule portions are push fitted over the tablet.

Figure 17:
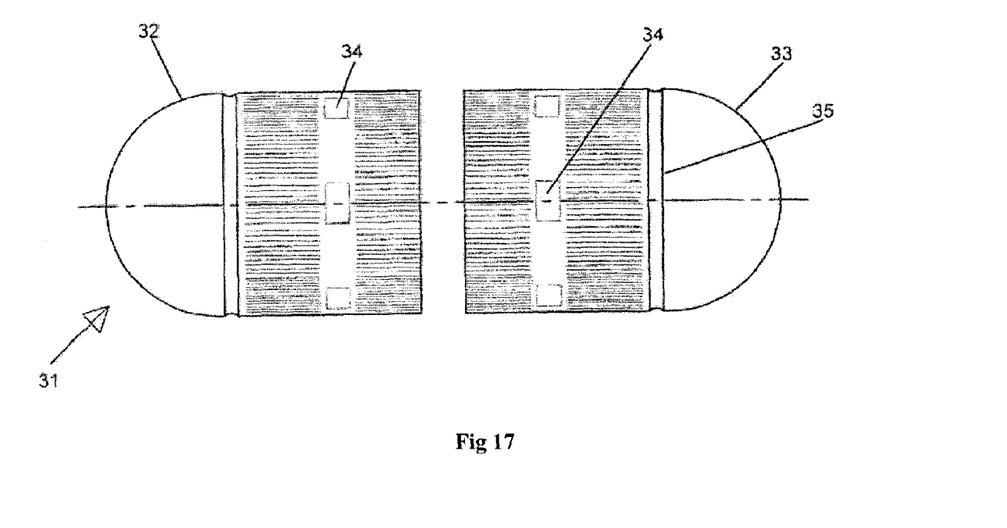
FIGS. 17 and 18 of the drawings accompanying the provisional specification are schematic elevation and longitudinal section of the two capsule portions of a capsule according to another embodiment of the invention, respectively.
Figure 18:
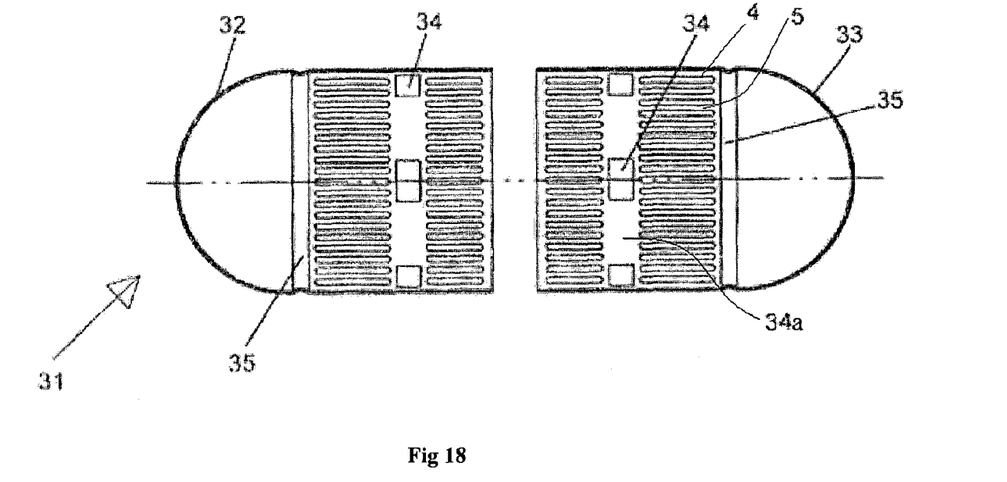

The capsule 31 as illustrated in FIGS. 17 and 18 of the drawings accompanying the provisional specification comprises two capsule portions 32 and 33. Each of the capsule portions further comprises a plurality of bulges 34 projecting inwardly from the inner circumference of the respective capsule portions in the space between two sets of ridges in radially spaced apart relationship with one another. Each of the capsule portions also comprises a circular protrusion 35 protruding inwardly from the inner circumference of the respective capsule portions in the proximity of the ridges and at the crown side of the respective capsule portions. The outlines defined by the centre of the bulges and the centre of the circular protrusion correspond to the outline defined by the tips of the ridges to provide further interference fit between the bulges and the circular protrusion and the tablet when the capsule portions are push fitted over the tablet. The spaces between the bulges define further fluid flow passages.

Figure 19:
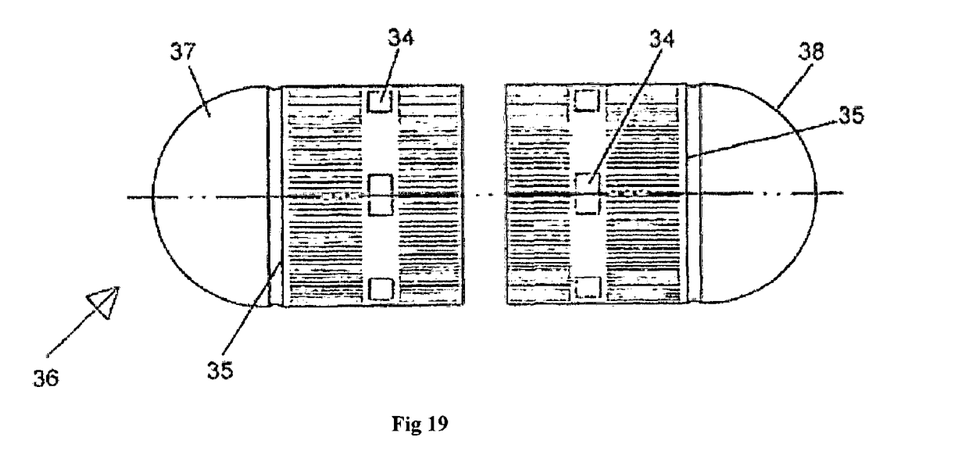
FIGS. 19 and 20 of the drawings accompanying the provisional specification are schematic elevation and longitudinal section of the two capsule portions of a capsule according to another embodiment of the invention.
Figure 20:
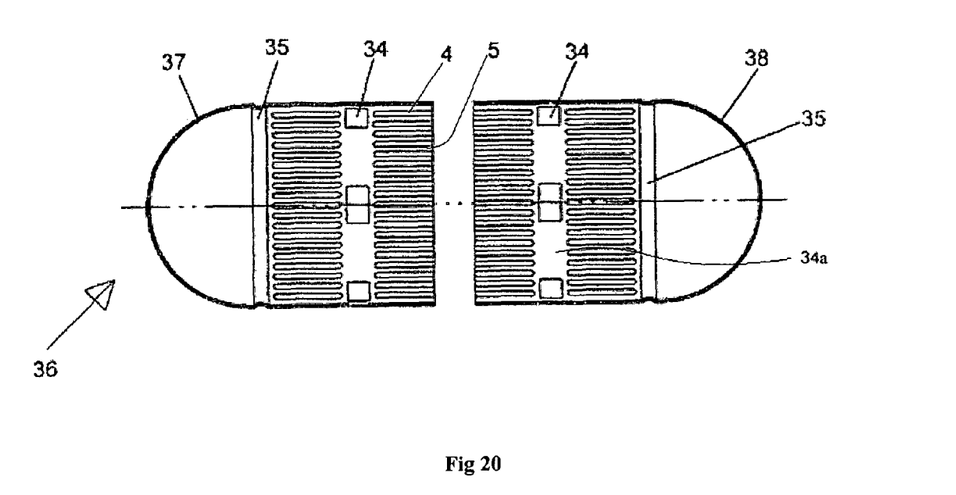

The capsule 36 comprising capsule portions 37 and 38 as illustrated in FIGS. 19 and 20 of the drawings accompanying the provisional specification is similar to the capsule of FIGS. 17 and 18 with the difference that one of the two sets of ridges at the open side of the capsule portions extend upto the edge of the open end of the capsule portions to define fluid flow passages between the ridges upto the edge of the open end of the capsule portions.

According to the invention the ridges and bulges in the capsule portions of capsules provide an interference fit between the capsule portions and tablet when the capsule portions are push fitted on the tablet from the ends of the tablet. The fluid flow passages in the capsule portions of capsules between the ridges and bulges allow air entrapped in the capsule portions to escape during encapsulation of tablets in the capsules. As a result, entrapment of air in the capsules and consequent damage to the capsules during encapsulation is prevented. On coming into contact with the body fluids in the stomach, the body fluids will enter the capsules via the hairline gap (capillary opening) between the abutting ends of the capsule portions and flow into the capsules easily through the fluid flow passages at the inner side of the capsule portions. This facilitates easy and fast disintegration and dissolution of the tablets in the body fluids. Furthermore, the dissolution pattern of the tablets can be modified by modifying the interference fit means in the capsule portions, for instance, by increasing the length and/or area of the fluid flow passages. The interference fit between the capsule portions and tablets ensures a tight fit between the capsule portions and the tablets.

Because of the low moisture content in the capsule portions, the capsules after encapsulation of the tablets do not require drying. Since the encapsulation is easy and convenient to carry out and does not require energy for drying, production time is reduced and productivity is increased. The interference fit means reinforce and give rigidity to the capsule portions. Because of this and because of the low moisture content in the capsule portions, the capsule portions are relatively hard. Therefore, the capsule portions do not collapse on the tablets and do not get damaged and/or deformed during encapsulation thereby retaining the shape and size and aesthetic look of the capsules. The capsules are also suitable for encapsulating both hydrophilic and hydrophobic tablets because of the relatively low moisture content in the capsule portions. The invention also does not require the rigid and harsh moisture conditions required in the prior art and is further easy and convenient to carry out.

As the capsule portions are in abutment when fitted on the tablets, the tablets are not exposed. The tablets are fully covered and do not require any masking or coating. As the capsule portions abut each other and the tablets are not exposed there is also no possibility for the tablets to get contaminated. Encapsulation carried out at ambient conditions further makes the invention energy efficient and convenient and easy to carry out. Capsule portions comprising the interference fit means are simple in construction and easy to mass produce and are economical.

The following comparative experimental studies are illustrative of the invention but not limitative of the scope thereof The dissolution rate of gelatin capsules comprising Acetaminophen or Paracetamol tablets (500 mg) encapsulated in gelatin capsule portions according to the invention and in conventional gelatin capsule portions was generated as per US Pharmacopia monograph procedure. The media used for the study was 5.8 pH phosphate buffer solution at 37±0.5° C. Volume of the media was 900 ml. The paddle assembly speed was 50 rpm.

Capsule portions of the invention used were those of FIGS. 4-6 of the accompanying drawings. Conventional capsule portions used were without the ridges and bulges. Gelatin composition for all the capsule portions was the same and the capsule halves had a moisture content of 14.3%. Encapsulation of the capsules according to the invention and conventional capsules was carried out by push fitting the capsule portions over the tablets from the ends of the tablets at ambient conditions in an abutting but not overlapping relationship with each other. Each experiment was conducted with 12 encapsulated capsules. The results were as shown in the following Table 1:

TABLE 1

| Experiment No | Capsule portions | Dissolution in 3 minutes | | | Dissolution in 5 minutes | | |
|---|---|---|---|---|---|---|---|
| | | minimum release (%) | maximum release (%) | average release (%) | minimum release (%) | maximum release (%) | average release (%) |
| 1. | Conventional | 28.03 | 39.32 | 33.68 | 65.07 | 71.75 | 66.99 |
| 2. | Conventional | 30.25 | 49.02 | 38.88 | 64.70 | 68.81 | 66.85 |
| 3. | Conventional | 19.36 | 41.14 | 31.90 | 51.42 | 78.07 | 62.24 |
| 4. | FIGS. 4-6 | 50.41 | 56.44 | 53.54 | 67.18 | 78.01 | 73.72 |
| 5. | FIGS. 4-6 | 50.27 | 53.52 | 51.84 | 69.25 | 76.65 | 72.34 |
| 6. | FIGS. 4-6 | 52.59 | 56.45 | 54.39 | 72.18 | 77.66 | 74.60 |

Table 1 clearly establishes that paracetamol encapsulated in capsules of the invention showed a very high dissolution rate as compared to paracetamol encapsulated in conventional capsules.

The above embodiments of the invention are only illustrative of the invention and are not limitative of the scope of the invention. The invention is essentially in the interface fit means at the inner circumference of the capsule portions to provide an interference fit between the capsules and tablets when the capsule portions are push fitted over the tablets and also to provide fluid flow passages for the air entrapped in the capsule portions to escape at the time of fitment of the capsule portions on the tablets and for the body fluids to easily flow into the capsule portions after the capsules are taken by the patients to facilitate disintegration and dissolution of the tablets swiftly. The geometry of the ridges can be different. The number of sets of ridges can be different. Configurational variations of the interference fit means with fluid passages but without deviating from the scope of the invention are possible. It is also understood that the tablets need not be pharmaceutical or neutraceutical substances but can be of any other material or substance. Such variations of the invention, which are obvious to a person skilled in the art are to be construed and understood to be within the scope of the invention. The scope of the invention is defined by and encompased within the following statement of claims.

The invention claimed is:

1. A capsule for encapsulating a tablet, comprising two capsule portions of equal sizes and dimensions, wherein the capsule portions contain a moisture content of 12 to 16% and the capsule portions each comprises interference fit means at the inner circumference thereof having a plurality of fluid flow passages therethrough and providing an interference fit between the capsule portions and the tablet when the capsule portions are push fitted over the tablet from the ends of the tablet in an abutting but not overlapping relationship with each other at ambient conditions, wherein the interference fit means comprises a plurality of ridges projecting inwardly from the inner circumference of the respective capsule portions and extending along the inner circumference of the respective capsule portions in radially spaced apart relationship with one another and defining the fluid flow passages between the ridges, the outline defined by the tips of the ridges corresponding to the outer surface of the tablet to provide an interference fit between the ridges and the tablet when the capsule portions are push fitted over the tablet.

2. The capsule as claimed in claim 1, wherein the capsule portions are push fitted over the tablet at 20-25° C.

3. The capsule as claimed in claim 1, wherein the capsule portions contain a moisture content of 12.5 to 14.5%.

4. The capsule as claimed in claim 1, wherein the capsule portions are made of gelatin, cellulose or starch.

5. The capsule as claimed in claim 1, wherein the interference fit means comprises a plurality of bulges projecting inwardly from the inner circumference of the respective capsule portions in the proximity of the plurality of ridges at the crown side of the capsule portions and in radially spaced apart relationship with one another, the outline defined by the centre of the bulges corresponding to the outline defined by the tips of the ridges to provide an interference fit between the bulges and the tablet when the capsule portions are push fitted over the tablet, the spaces between the bulges also defining fluid flow passages.

6. The capsule as claimed in claim 1, wherein the interference fit means comprises a plurality of bulges projecting inwardly from the inner circumference of the respective capsule portions at an intermediate position of the ridges in radially spaced apart relationship with one another and a circular protrusion protruding inwardly from the inner circumference of the respective capsule portions at the crown side of the respective capsule portions in the proximity of the ridges, the outline defined by the centre of the bulges and the centre of the circular protrusion corresponding to the outline defined by the tips of the ridges to provide an interference fit between the bulges and the circular protrusion and the tablet when the capsule portions are push fitted over the tablet, the spaces between the bulges also defining fluid flow passages.

7. The capsule as claimed in claim 1, wherein the ridges extend upto the edge of the open end of the respective capsule portions.

8. The capsule as claimed in claim 1, wherein the ridges extend upto the edge of the open end of the respective capsule portions and the interference fit means comprises a plurality of bulges projecting inwardly from the inner circumference of the respective capsule portions in the proximity of the plurality of ridges at the crown side of the capsule portions and in radially spaced apart relationship with one another, the outline defined by the centre of the bulges corresponding to the outline defined by the tips of the ridges to provide an interference fit between the bulges and the tablet when the capsule portions are push fitted over the tablet, the spaces between adjacent bulges defining fluid flow passages.

9. The capsule as claimed in claim 1, wherein the ridges extend upto the edge of the open end of the respective capsule portions and the interference fit means comprises a plurality of bulges projecting inwardly from the inner circumference of the respective capsule portions at an intermediate position of the ridges in radially spaced apart relationship with one another and a circular protrusion protruding inwardly from the inner circumference of the capsule portions at the crown side of the respective capsule portions in the proximity of the ridges, the outline defined by the centre of the bulges and centre of the circular protrusion corresponding to the outline defined by the tips of the ridges to provide an interference fit between the bulges and the circular protrusion and the tablet when the capsule portions are push fitted over the tablet, the spaces between adjacent bulges also defining fluid flow passages.

10. A capsule for encapsulating a tablet, comprising two capsule portions of equal sizes and dimensions, wherein the capsule portions contain a moisture content of 12 to 16% and the capsule portions each comprises interference fit means at the inner circumference thereof having a plurality of fluid flow passages therethrough and providing an interference fit between the capsule portions and the tablet when the capsule portions are push fitted over the tablet from the ends of the tablet in an abutting but not overlapping relationship with each other at ambient conditions, wherein the interference fit means comprises two sets of ridges extending along the inner circumference of the respective capsule portions spaced apart from each other along the length of the inner circumference of the capsule portions, each set of ridges comprising a plurality of ridges projecting inwardly from the inner circumference of the respective capsule portions in radially spaced apart relationship with one another and defining the fluid flow passages between the ridges, the outline defined by the tips of each set of ridges corresponding to the outer surface of the tablet to provide an interference fit between the ridges and the tablet when the capsule portions are push fitted over the tablet, the spaces between the two sets of ridges also defining fluid flow passages.

11. The capsule as claimed in claim 10, wherein the interferences fit means comprises a plurality of bulges projecting inwardly from the inner circumference of the respective capsule portions in the space between the two sets of ridges in radially spaced apart relationship with one another and a circular protrusion protruding inwardly from the inner circumference of the respective capsule portions in the proximity of the ridges and at the crown side of the respective capsule portions, the outline defined by the centre of the bulges and the centre of the circular protrusion corresponding to the outline defined by the tips of the ridges to provide an interference fit between the bulges and circular protrusion and the tablet when the capsule portions are push fitted over the tablet, the spaces between the adjacent bulges and between the sets of ridges also defining fluid flow passages.

12. The capsule as claimed in claim 10, wherein one of the two sets of ridges at the open side of the capsule portions extend upto the edge of the open end of the respective capsule portions, and the interference fit means comprises a plurality of bulges projecting inwardly from the inner circumference of the respective capsule portions in the space between the two sets of ridges in radially spaced apart relationship with one another and a circular protrusion protruding inwardly from the inner circumference of the respective capsule portions in the proximity of the ridges and at the crown side of the respective capsule portions, the outline defined by the tips of the ridges and the centre of the bulges and the centre of the circular protrusion corresponding to the outer surface of the tablet to provide an interference fit between the ridges, bulges and circular protrusion and the tablet when the capsule portions are push fitted over the tablet, the spaces between adjacent bulges and between the sets of ridges defining fluid flow passages.

13. The capsule as claimed in claim 10, wherein the capsule portions are push fitted over the tablet at 20-25° C.

14. The capsule as claimed in claim 10, wherein the capsule portions contain a moisture content of 12.5 to 14.5%.

15. The capsule as claimed in claim 10, wherein the capsule portions are made of gelatin, cellulose or starch.

* * * * *